United States Patent [19]

Albery et al.

[11] 4,400,242
[45] Aug. 23, 1983

[54] ELECTROCHEMICAL METHOD OF DETERMINING OXYGEN, HALOTHANE AND NITROUS OXIDE

[75] Inventors: Wyndham J. Albery, London; Clive E. W. Hahn, Abingdon, both of England

[73] Assignee: National Research Development Corporation, London, England

[21] Appl. No.: 355,139

[22] Filed: Mar. 5, 1982

Related U.S. Application Data

[63] Continuation-in-part of Ser. No. 190,257, Sep. 24, 1980, abandoned.

[30] Foreign Application Priority Data

Sep. 24, 1979 [GB] United Kingdom ............... 7933007

[51] Int. Cl.³ ............................................ G01N 27/54
[52] U.S. Cl. .................................... 204/1 T; 204/415
[58] Field of Search .......... 204/1 P, 1 B, 1 N, 195 P; 128/635

[56] References Cited

U.S. PATENT DOCUMENTS 4,077,861  3/1978  Lauer ................................. 204/402

FOREIGN PATENT DOCUMENTS 2657351  7/1977  Fed. Rep. of Germany ...... 204/415
2832501  8/1979  Fed. Rep. of Germany ...... 204/415
1200595  7/1970  United Kingdom ............ 204/195 P

OTHER PUBLICATIONS

Smirnov, P.N.; "Fluorothane" appearing in *Soviet Inventions Illustrated*—Mar., 1963.

Hahn, C. E. W. et al., "$O_2$ and $N_2O$ Analysis with a Single Intravascular Catheter Electrode"—*Anesthesia*, 1979, vol. 34, pp. 263-264, 1979.

Brooks, W. N. et al., "The Simultaneous Measurement of $PO_2$ and $PN_2O$ In Vivo with a Single Catheter Intravascular Electrode", (Preliminary Report)—*British Journal of Anesthesia*.

Albery, W. J. et al.–"An Electroanalytical Method for the Determination of $N_2O$"-*Electro Chimica Acta*, vol. 4, pp. 107 and 108-1979.

W. J. Albery et al., *J. Appl Physiology*, vol. 45, pp. 637-643, (1978).

*Primary Examiner*—G. L. Kaplan
*Attorney, Agent, or Firm*—Cushman, Darby & Cushman

[57] ABSTRACT

In a method of electrochemically sensing the presence of $O_2$, $N_2O$ and halothane in a fluid, a gold or platinum electrode and a silver electrode are exposed to the fluid through a permeable membrane.

both electrodes are held at a first potential and the currents due respectively to reduction of oxygen at the gold or platinum electrode and reduction of oxygen and halothane at the silver electrode are sensed, the silver electrode is held at a second potential and the current due to reduction of oxygen and halothane and nitrous oxide is sensed, and from the three currents the presence and/or concentration of any of the three gases is determined.

2 Claims, 8 Drawing Figures

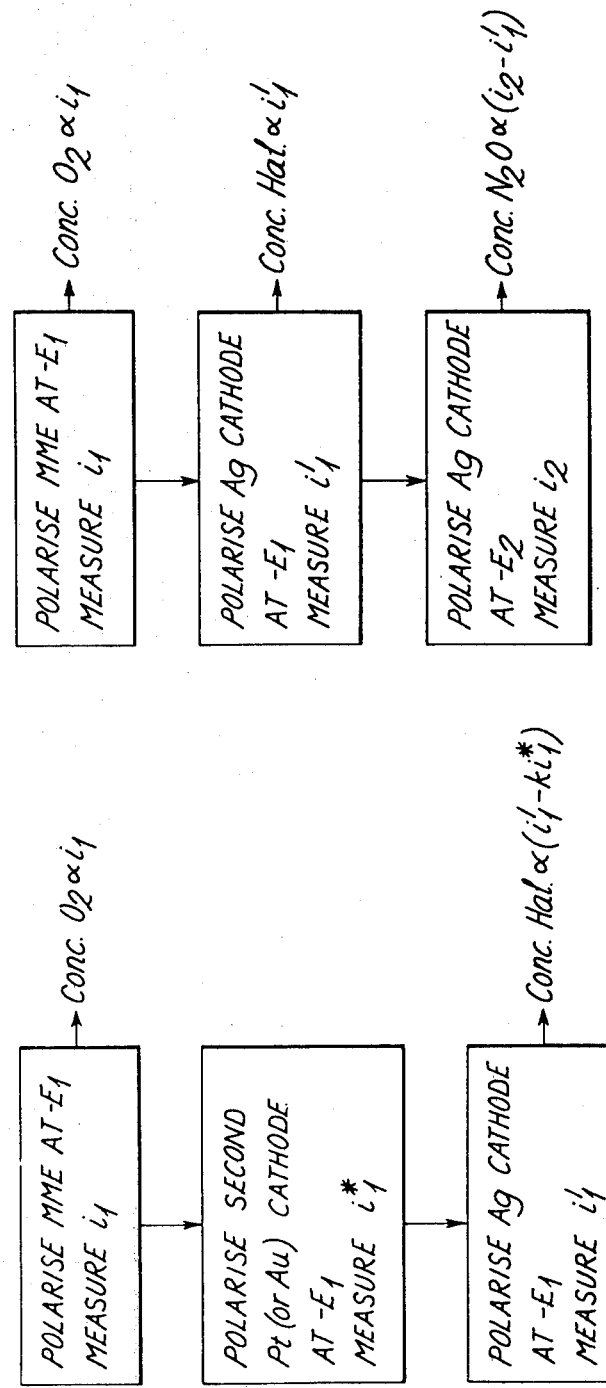

ELECTROCHEMICAL METHOD OF DETERMINING OXYGEN, HALOTHANE AND NITROUS OXIDE

This application is a continuation-in-part of application Ser. No. 190257 filed on 24th September 1980 and now abandoned.

It has been known for some time that the presence and concentration of oxygen and nitrous oxide, for example in a stream of anaesthetic gas or in the blood of an anaesthetised animal, can be distinguished polarographically by use of a silver electrode, and their separate concentrations measured. This is described in Journal of Applied Physiology 45 (4), pages 637 to 643, 1978, in a paper by Albery, Brooks, Gibson and Hahn. It is also known that halothane (1-bromol-chloro2,2,2-trifluoroethane) can be sensed polarographically by use of a dropping mercury electrode, see Soviet Inventions Illustrated, March 1963 page 6, but previously it has not been possible to distinguish the presence of the three gases in a fluid or to determine their concentrations separately.

According to the invention, a method of electrochemically sensing the presence of oxygen and nitrous oxide and halothane in a fluid comprises exposing a gold or platinum electrode and a silver electrode to the fluid through permeable means through which gases from the fluid can pass, both electrodes being in contact with an electrolyte;

holding the gold or platinum electrode at a first potential such that oxygen is reduced at that electrode, and sensing any first current flowing through the gold or platinum electrode;

holding the silver electrode at said first potential such that oxygen and halothane are reduced at their electrode, and sensing any second current flowing through the silver electrode;

subsequently holding the silver electrode at a second potential such that oxygen and halothane and nitrous oxide are reduced at that electrode and sensing any third current flowing through the silver electrode;

and from the three currents determining whether any (or all) of the three gases are present.

In a modification, the magnitudes of the three currents and therefore the concentrations of any or all three gases are determined.

Also according to the invention, an electrochemical sensor for sensing the presence of oxygen and nitrous oxide and halothane in a fluid comprises a gold or platinum electrode;

a silver electrode;

a container for an electrolyte which when present contacts the two electrodes;

permeable means through which gases from the fluid can pass to the electrodes;

circuit means for holding the gold or platinum electrode and the silver electrode at a first potential such that oxygen is reduced at the gold or platinum electrode and oxygen and halothane are reduced at the silver electrode and cause respective first and second currents to flow through the electrodes, and for holding the silver electrode subsequently at a second potential such that oxygen and nitrous oxide and halothane are reduced at the silver electrode and cause a third current to flow through that electrode;

and current sensing means for sensing the presence of each of the three currents.

In a first arrangement, the platinum or gold electrode and the silver electrode are of relatively small surface area; for example, they may be in the form of the endfaces of metal wires. The magnitude of the first current is proportional to the concentration of oxygen, the difference between the second and first currents is proportional to the concentration of halothane, and the difference between the third and second currents is proportional to the concentration of nitrous oxide.

In a second arrangement, the platinum or gold electrode is in the form of a relatively large area of metallised membrane, any gas in the fluid passes through the membrane to the silver electrode and any oxygen present is entirely reduced at the membrane electrode. The first current is then proportional to oxygen concentration, the second current is proportional to halothane concentration and the difference between the third and second currents is proportional to nitrous oxide concentration.

In a third arrangement, the platinum or gold electrode is in the form of a metallised membrane, the gas from the fluid passes through the membrane to the silver electrode and a substantial proportion less than one hundred per cent of any oxygen present is reduced at the membrane electrode. In this arrangement there is provided a second platinum or gold electrode which is contacted by the gas in the fluid after passage of the gas through the membrane electrode; this second platinum or gold electrode is held at the first potential and any fourth current flowing through it is determined. The first current is then proportional to the oxygen concentration, the difference between the second current and the fourth current multiplied by a factor less than one is proportional to the halothane concentration, and the difference between the third and second currents is proportional to nitrous oxide concentration.

As an alternative of the third arrangement there is provided in the apparatus between the metallised membrane and the silver electrode a chemical system capable of reducing all of the oxygen passing through the metallised membrane while allowing the electrochemical reactions to continue. An example of such a chemical system is a solution of a suitable hydroquinone.

In a method and apparatus according to the invention, the electrochemical reduction of nitrous oxide at the silver electrode produces nitrogen as a reaction product. If the silver electrode is held at the second potential for prolonged periods, bubbles of nitrogen will form, will occlude the cathode, and will seriously interfere with the gas sensing process.

It is a further feature of the invention that the second potential is applied to the silver electrode as a series of pulses and that the resultant transient current through the silver electrode is sensed at a predetermined time after the beginning of the application of each pulse. Usually the time of measurement will be such that a steady state current will not have been attained, but a known proportion of the steady state level will have been reached, allowing accurate measurement of the gas concentrations. Conveniently, the first potential is applied continuously to both the platinum or gold electrode and the silver electrode, a series of pulses being superimposed to change the potential of the silver electrode intermittently to the second value. The currents through the silver electrode are measured at predetermined time intervals after the beginning and end of each superimposed pulse.

The invention will now be described by way of example with reference to the accompanying drawings in which:

FIGS. 5 and 6 are schematic diagrams indicating two possible types of operation of the FIG. 3 device;

Figure 8:
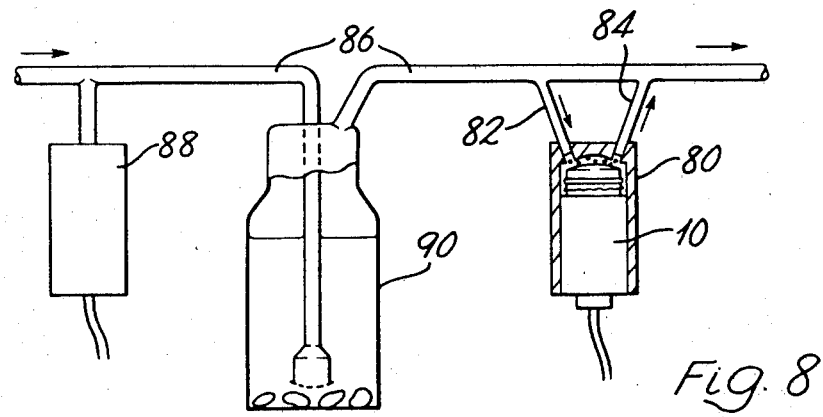

FIG. 8 indicating use of the first embodiment in conjunction with an oxygen scrubber.

It is well known that oxygen can be sensed polarographically at an electrode made of platinum or gold or silver and held at the appropriate electrochemical potential at which oxygen is reduced. It is also known that nitrous oxide cannot be detected polarographically at a platinum or gold electrode, but can be detected at a silver electrode; the silver catalyses reduction of the gas. We have now discovered that halothane can also be sensed at a silver electrode, which catalyses its reduction, but, rather surprisingly, not at a platinum electrode. We have further discovered that halothane is reduced at a gold electrode at rather negative voltages, but that at less negative voltages there is no reduction of halothane and at these potentials gold behaves like platinum. We have applied this discovery in our inventive method and apparatus for sensing the presence in a fluid of all three gases, and for determining their individual concentrations.

Figure 1:
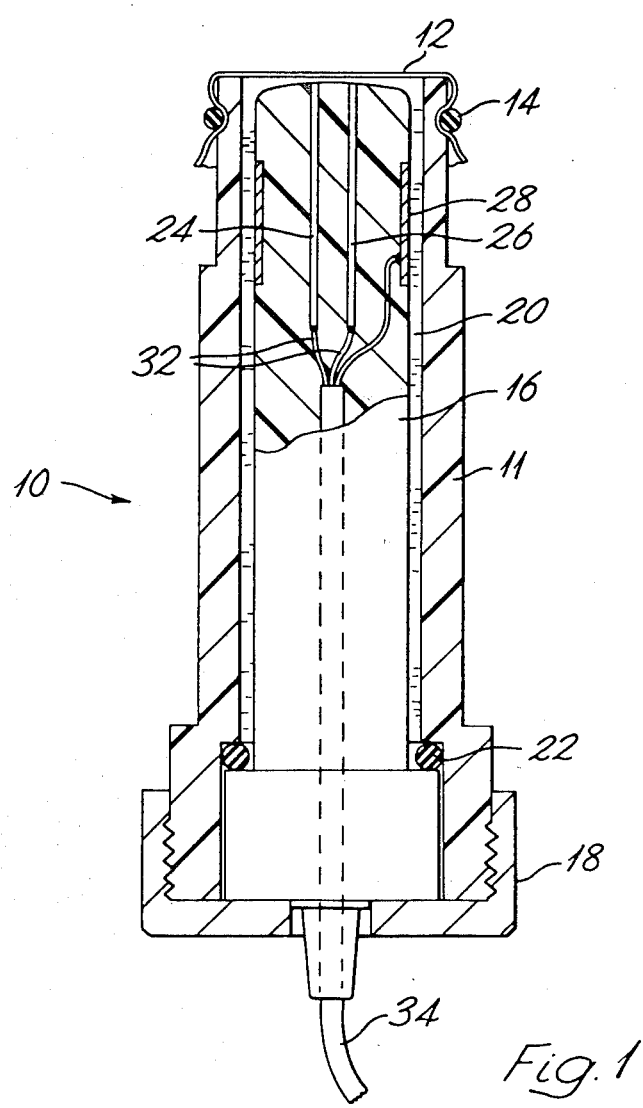
FIG. 1 is a section through a first embodiment of a gas sensor according to the invention.

In FIG. 1, a gas sensor 10 comprises an outer tubular holder 11 closed at one end by a membrane 12 which is secured by an "O" ring 14. The membrane is permeable to oxygen and halothane and nitrous oxide, and may for example for made of silastic.

Within the outer holder is an insulating body 16 (conveniently of cast epoxy resin) held in place by a screw cap 18. The holder 11 and body 16 are of such relative diameters that there is a space between them. This space is filled with an electrolyte 20, such as an aqueous solution of IM potassium hydroxide and 0.1M potassium chloride. The body 16 carries a platinum wire cathodde 24 and a silver wire cathode 26, the ends of the wires being flush with the end of the body 16 and spaced a short distance from the membrane 12. The body 16 also carries a cylindrical band of silver 28, having its cylindrical surface flush with the side of the body and in contact with the electrolyte 20 to form a silver/silver chloride reference electrode. The three electrodes are connected via connections 32 passing through a central aperture in the body 16 and via a connecting cable 34 which passes through the screw cap 18 to a control measuring circuit (not illustrated in FIG. 1).

In use, the membrane 12 of the electroe system is exposed to a fluid to be tested; gases in the fluid to which the membrane is permeable diffuse through the membrane and into the electrolyte 20. If the platinum cathode 24 is held at a potential $E_1$ of about $-0.80$ volts then any oxygen reaching the cathode will be reduced, and a current $i_1$ proportional to the concentration of that oxygen will pass through the cathode. If the silver cathode 26 is held at the same potential $E_1$, oxygen and halothane reaching that electrode will be reduced and a current $i_1'$ proportional to the concentration of those gases (bearing in mind the different sensitivities to the two gases of the electrode) will pass through the silver cathode. The concentration of halothane in the electrolyte 20 can be determined from the difference between the currents $i_1' - i_1$.

If the silver electrode 26 is then held at a potential $E_2$ of about $-1.4$ volts all three gases will be reduced and a current $i_2$ will flow; the difference $i_2 - i_1'$ gives a measure of the concentration of nitrous oxide.

Figure 2:
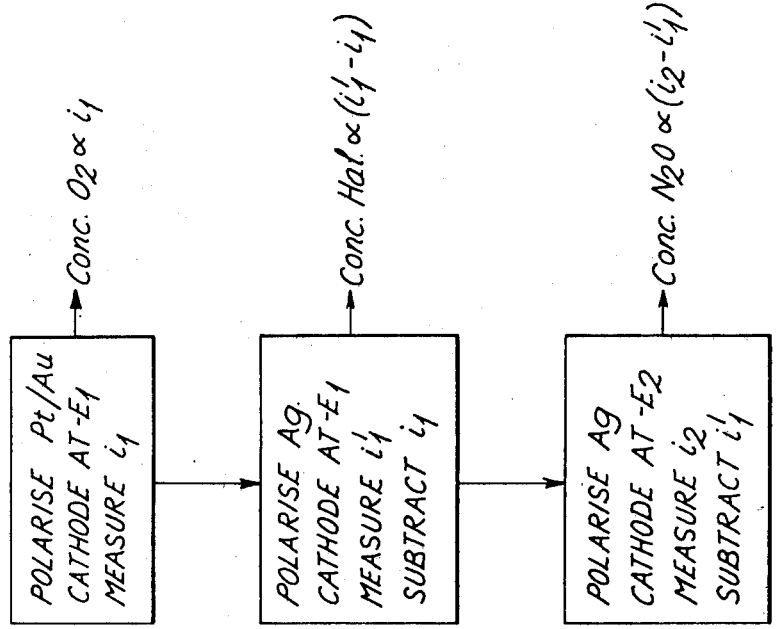
FIG. 2 is a schematic diagram indicating the operation of the FIG. 1 device.

The current relationships described are illustrated in FIG. 2.

The concentration of the gases which diffuse through the membrane depend on the concentration in the fluid under test and the partition coefficients between the fluid and the membrane and between the membrane and the electrolyte. When the cathodes 24, 26, are polarised and a steady state reached, a concentration gradient is established between the cathode surface, where the surface concentration of the reactive gas or gases is effectively zero, and the fluid under test. The currents through the cathodes are therefore proportional to the rate of diffusion of the reactive gas down the concentration gradient, and thus to the concentration in the fluid under test. The instrument can therefore be calibrated before use.

Since the potential required for reduction of nitrous oxide is highly cathodic, a highly basic electrolyte must be used to enable a limiting current to be reached and measured, otherwise the electrolyte would decompose to evolve hydrogen at a potential less cathodic than that for $N_2O$ reduction.

A measurement according to the invention is made on an electrochemical current plateau and is therefore not sensitive to minor changes in potential. Application of a d.c. potential from a stable source gives a sufficiently constant polarising voltage without the need to use a reference electrode. However, a third, reference, electrode 28 can be provided as in conventional electrochemical devices if circumstances require a very precise polarising voltage.

If the platinum wire electrode 24 is replaced by a gold wire electrode, then at certain polarising voltages the reduction of halothane will not be catalysed by the gold electrode. For example, at a voltage of $-0.6$ volts and a pH of 13 halothane will not be reduced and the gold electrode can be used to measure the oxygen current $i_1$. As described above, subtraction of this current from the current on a silver electrode gives the halothane concentration. However, at a voltage of $-0.8$ halothane would be reduced on a gold electrode and could not be sensed separately from oxygen, and this condition must be avoided. It should be noted that the precise voltages are pH dependent.

Figure 3:
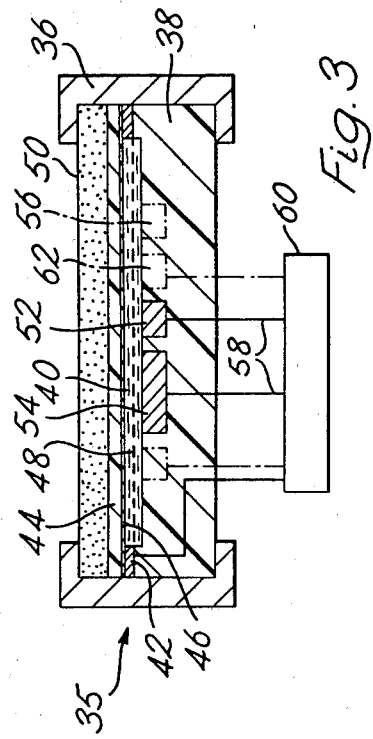
FIG. 3 is a section through and FIG. 4 is a plan view of a second embodiment.

An alternative embodiment 35 using a large-area metallised membrane electrode is illustrated in FIG. 3. An outer cylindrical cover 36 houses a solid disc-shaped body 38, both of insulating material. The body 38 has in its upper face a depression which can hold an electrolyte 40. A ring-shaped metal contact 42 lies on the upper surface of the disc around the electrolyte depression and supports a gold or platinum metallised membrane electrode 44; the metallised face 46 of the electrode is in contact with the metal ring 42. The electrolyte depression also contains a nylon mesh spacer 48 which helps to support the lever face of the membrane electrode 44, and a sintered metal disc 50 is held by the cover 36 to protect the upper face of electrode 44. The electrolyte depression contains sufficient electrolyte 40 to contact the metal face of the membrane electrode.

Figure 4:
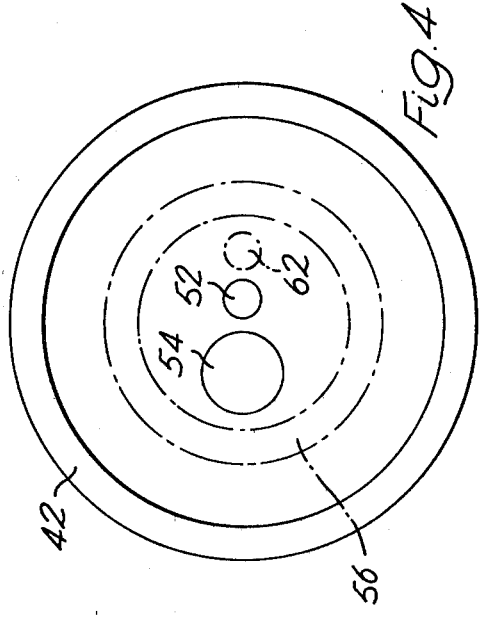

The body 38 carries two electrodes with their upper faces flush with the upper surface of the body. As shown in FIG. 4, there is a centrally placed cylindrical silver electrode 52 and an adjacent cylindrical silver/silver chloride reference electrode 54. External connections 58 to these two electrodes and to the metallised membrane contact 42 are shown schematically; the connections pass to a suitable control and measuring circuit 60.

The metallised membrane electrode 44 must be of a material which is permeable to the three gases to be detected. A suitable construction is described in the specification of UK Pat. No. 1,200,595, in which a permeable membrane is covered with a layer of sputtered gold.

When the device 35 is exposed to a gaseous atmosphere, gas passes through the sintered metal disc 50 and through both layers 44, 46 of the metallised membrane electrode to the interface between the gold or platinum and the electrolyte 40. When the electrode 46 is held at a potential $-E_1$, oxygen is reduced at the interface and a current $i_1$ flows through the electrode which is proportional to the oxygen concentration. The rate of diffusion of the gas through the membrane and the metallisation of the electrode 46 can be chosen so that all of the oxygen reaching the electrode is removed and no oxygen reaches the silver cathode 52.

It has been found that a membrane electrode with a gold layer is not only robust and relatively easy to manufacture, but is very effective when used as an oxygen "filter" as described above.

If the silver cathode is held at the potential $-E_1$, any current $i_1'$ flowing through it is proportional to the concentration of halothane. If the silver cathode 52 is subsequently held at a potential $-E_2$ volts, both halothane and nitrous oxide are reduced and the corresponding current $i_2$ can be used to calculate the concentration of nitrous oxide by difference. The potential and current relationships are illustrated in FIG. 5.

If, however, the efficiency of oxygen removal by the metallised membrane electrode is not 100%, some oxygen will reach the silver cathode 52 and be reduced at that electrode at both the applied potentials $E_1$ and $E_2$. This problem can be overcome by inclusion of an additional platinum or gold electrode 62 (shown dotted in FIGS. 3 and 4), similar in position to the reference electrode 54. The additional electrode 62 would also be connected to the electronic circuit, which would be of modified form to allow for the different current relationships described below and illustrated in FIG. 6.

Although not all of the oxygen is removed at the membrane electrode, the current $i_1$ through this electrode is still proportional to oxygen concentration. The additional electrode 62 is also polarised at potential $E_1$ and oxygen reaching this electrode causes a current $i_1^*$ to flow. Some oxygen also reaches the silver cathode 52, and at potential $E_1$ the current $i_1'$ through this electrode corresponds to the reduction of halothane plus reduction of some of the residual oxygen. The true concentrations of halothane can be derived by subtracting from $i_1'$ the current $i_1^*$, multiplied by a factor k where k depends on the relative areas of the membrane electrode 44 and the silver cathode 52. When the silver cathode is held at potential $E_2$, the current $i_2$ corresponds to reduction of nitrous oxide and halothane and of part of the residual oxygen; the concentration of nitrous oxide can be determined from the difference between $i_2$ and $i_1'$.

In either of the embodiments described above, the silver cathode cannot be polarised at the potentials $E_2$ at which nitrous oxide is reduced for prolonged periods, because nitrogen is produced as a reaction product; in time, bubbles will form and occlude the cathode.

To overcome this problem, in further aspect of the present invention, the polarising voltage $E_2$ is applied to the silver cathode as a series of pulses. It has been found that application of a pulsed polarising voltage results in the advantages of greater sensitivity, lack of a stirring effect, and independence of the current from the thickness and material of the metallised membrane electrode 44, 46.

Figure 7:
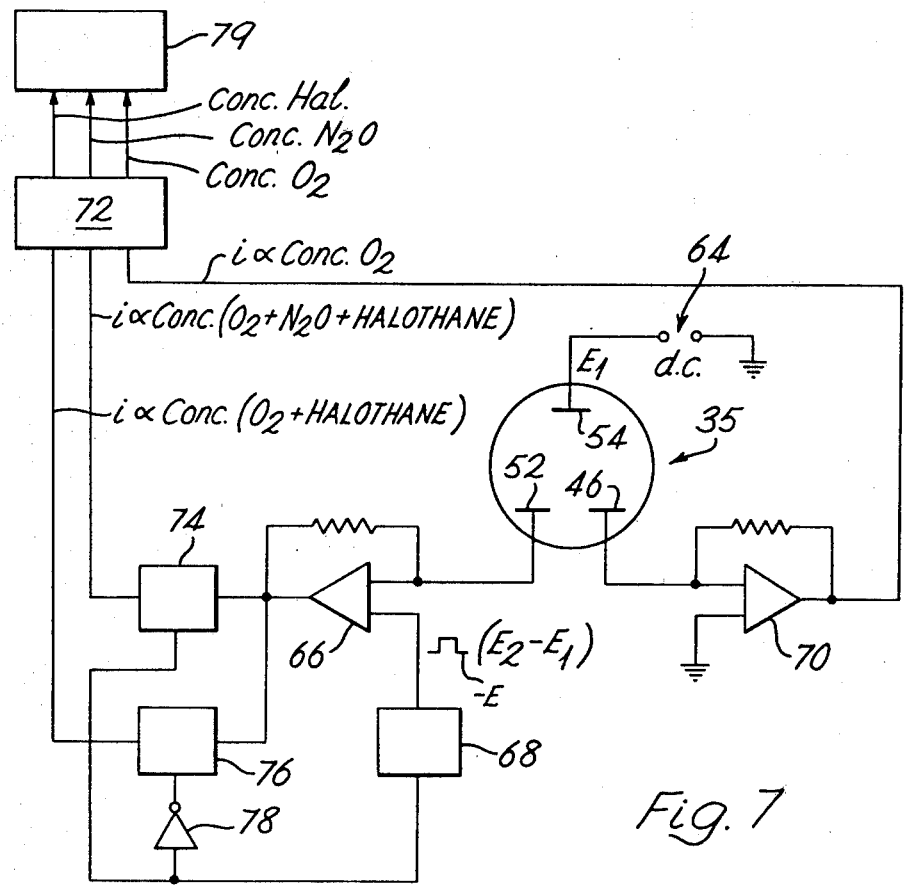
FIG. 7 is a diagram of a suitable associated electronic circuit.

A suitable circuit diagram is illustrated in FIG. 7. The sensor 35 is shown in highly schematic form having a platinum or gold metallised membrane electrode 46, silver cathode 52 and silver/silver chloride reference electrode 54.

The reference electrode 54 is connected to the positive side of a stable d.c. power source, which holds the cathodes 46, 52 at the required steady negative voltage $E_1$ volts. The silver cathode 52 is connected to the inverting input of a first operational amplifier 66, the non-inverting input being connected to a pulse generator 68 which provides square pulses which intermittently change the potential of the silver cathode 52 to the more negative potential $E_2$.

The platinum or gold cathode 46 is connected to the inverting input of a second operational amplifier 70, the non-inverting input being earthed and the output being connected to an arithmetic unit 72. This amplifier is used to sense any current through the cathode 46. Similarly the first amplifier 66 senses any current through the silver cathode 52, and the amplifier output is connected through two sample and hold units 74, 76 to the arithmetic unit 72. The units 74, 76 are gated by the pulse generator 68, one of them through an inverter 78, so that the output of amplifier 66 is sampled alternately by the units at predetermined intervals after the beginning and end of each pulse from the pulse generator, the outputs corresponding to the transient currents through the silver cathode 52 at voltages $E_1$ and $E_2$. The current values are held and supplied to the arithmetic unit 72 which, by application of suitable sensitivity factors, performs the required subtractions and provides three output signals, respectively proportional to the concentrations of the three gases. These signals can, if required, be averaged over a predetermined number of pulses and displayed on a display device 79 of any suitable type.

The circuit illustrated in FIG. 7 can be used in conjunction with either the FIG. 1 or the FIG. 3 embodiment of the invention.

Reference has already been made to the fact that, of the three gases which can be detected according to the invention, it will usually be the case that the concentration of oxygen will be greater, perhaps by a factor of about ten, than the concentration of halothane; typical values are 70% $N_2O$; 29% $O_2$; and 1% halothane. The possibility of removing all oxygen by a metallised membrane electrode before it reaches the silver cathode has been described with reference to FIG. 3. If however the circumstances are such that the oxygen cannot be removed entirely by an electrochemical reaction, it is possible to provide in the electrolyte 40 of the FIG. 3 embodiment a chemical system capable of removing any oxygen which passes through the metallised membrane electrode 44, 46.

A driver electrode is provided, reference 56, in the form of a ring of silver surrounding the silver cathode 52 and reference electrode 54. The additional electrode 62 is not required. This driver electrode is connected to a modified form of the electronic circuit 60 which holds the electrode at a required steady potential.

In addition to the electrolyte of potassium hydroxide and potassium chloride, there is further provided a solution of 1-8 dihydroxy anthroquinone which, driven by the driver elecdtrode, reacts with water to provide the hydroquinone form, the reaction being:

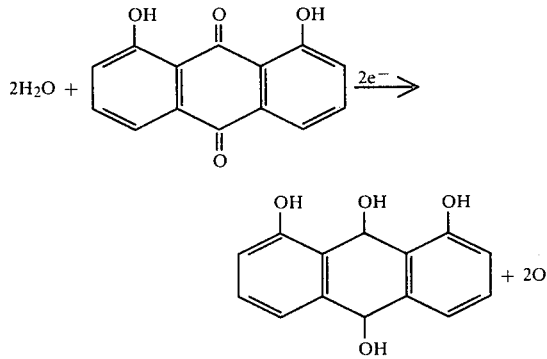

The hydroquinone then reacts with any oxygen in the electrolyte according to the equation:

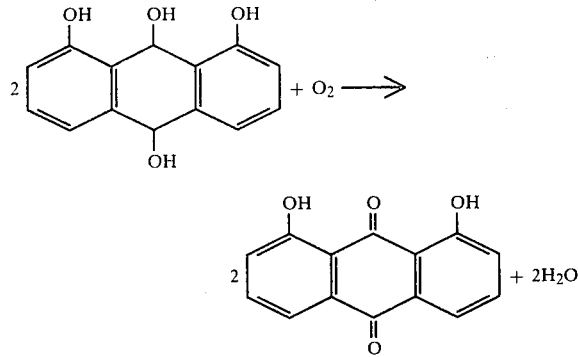

removing all oxygen reaching the electrolyte.

The anthroquinone is again reduced to the hydroquinone form to maintain the supply. These chemical reactions do not affect the electrochemical measurements. The current through the silver cathode is then proportional only to nitrous oxide or to nitrous oxide and halothane, depending on the polarising voltage, with no contribution from oxygen. The current through the metallised membrane will still be proportional to oxygen concentration, even though it does not remove all of the oxygen entering the device.

A similar chemical reaction can be used in conjunction with the embodiment illustrated in FIG. 1; as shown in FIG. 8, the outer holder 10 is held in a fixture 80 having an inlet tube 82 and outlet tube 84 to a gas pipe 86. Gas from a source (not shown) passes first to an oxygen sensor 88 for conventional type and then through an oxygen scrubber 90, illustrated as a Drechsel bottle containing a solution of an alkaline anthraquinone-2-sulphonate, such as the sodium salt, and zinc amalgam. In the reaction:

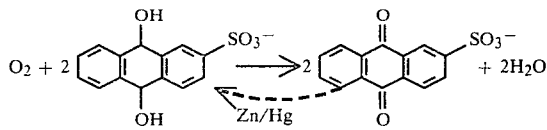

any oxygen in the gas flowing along the pipe is removed, and the zinc amalgam reduces the quinone form back to the hydroquinone form. Oxygen will be absorbed until all of the amalgam is used up, and only halothane and nitrous oxide will reach the sensor 10. In this arangement the driver electrode must be made of platinum or gold to avoid reduction of halothane. There will be no current through the platinum or gold cathode 24 if the oxygen scrubber is operating efficiently; the cathode 24 can therefore be used to check the efficiency.

An oxygen scrubber could also be used in conjunction with the embodiment illustrated in FIG. 3.

It is expected that the method and apparatus of the invention will find their main use in gas measurements in anaesthetic apparatus and hospital gas supply lines, but they can aslo be used *in vitro* blood-gas analysis and *in vivo* measurements using either a catheter or a transcutaneous sensing arrangement. Industrial applications are also possible.

We claim:

1. A method of electrochemically sensing the presence of oxygen and nitrous oxide and halothane in a fluid comprises exposing a gold or platinum electrode and a silver electrode to the fluid through permeable means and an electrode-contacting electrolyte through which gases from the fluid can pass, holding the gold or platinum electrode at a first potential such that oxygen is reduced at that electrode and sensing any first current flowing through the gold or platinum electrode;

holding the silver electrode at said first potential such that oxygen and halothane are reduced at that electrode and sensing any second current flowing through the silver electrode;

subsequently holding the silver electrode at a potential such that oxygen and halothane and nitrous oxide are reduced at that electrode and sensing any third current flowing through the silver electrode;

and from the three currents determining whether any of the three gases are present.

2. A method according to claim 1 in which magnitudes of the three currents are measured and the concentrations of any of the three gases present are determined.

* * * * *